US00PP17634P3

(12) United States Plant Patent
Gossett

(10) Patent No.: US PP17,634 P3
(45) Date of Patent: Apr. 24, 2007

(54) ×*HEUCHERELLA* PLANT NAMED 'HERTN041'

(50) Latin Name: ×*Heucherella* sp.
Varietal Denomination: HERTN041

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 142 days.

(21) Appl. No.: 11/088,695

(22) Filed: Mar. 22, 2005

(65) Prior Publication Data

US 2006/0218687 P1 Sep. 28, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Georgia Helmer
(74) *Attorney, Agent, or Firm*—Klarquist Sparkman, LLP

(57) ABSTRACT

A new and distinct cultivar of ×*Heucherella* plant substantially as shown and described, characterized by its distinctive soft yellow to lime green foliage with speckles of maroon along the veins and distinctive lobing.

2 Drawing Sheets

Botanical denomination: ×*Heucherella* sp.
Variety designation: 'HERTN041'.

BACKGROUND OF THE INVENTION

The present invention relates to a new and distinct intergeneric hybrid between *Heuchera* and *Tiarella,* and botanically called ×*Heucherella.* This new variety is given the cultivar name 'HERTN041'. Both genera, *Heuchera* and *Tiarella,* are of the family Saxifragaceae.

The claimed plant resulted from crossing *Heuchera* 'Amber Waves' (U.S. Plant Pat. No. 13,348), as the seed parent, with massed pollen from a group of experimental, proprietary *Tiarella* hybrids. As such, the exact pollen parent is unknown.

SUMMARY OF THE INVENTION

This new *Heucherella* is unique in its soft yellow foliage with specked, maroon markings along the main veins and is also characterized by:

1. Small, 5-lobed leaves.
2. Unusual white flowers on numerous, short stalks.

The new variety has been reproduced only by sexual propagation (division and tissue culture). Each of the progeny exhibits identical characteristics to the original plant. Asexual propagation by division and tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
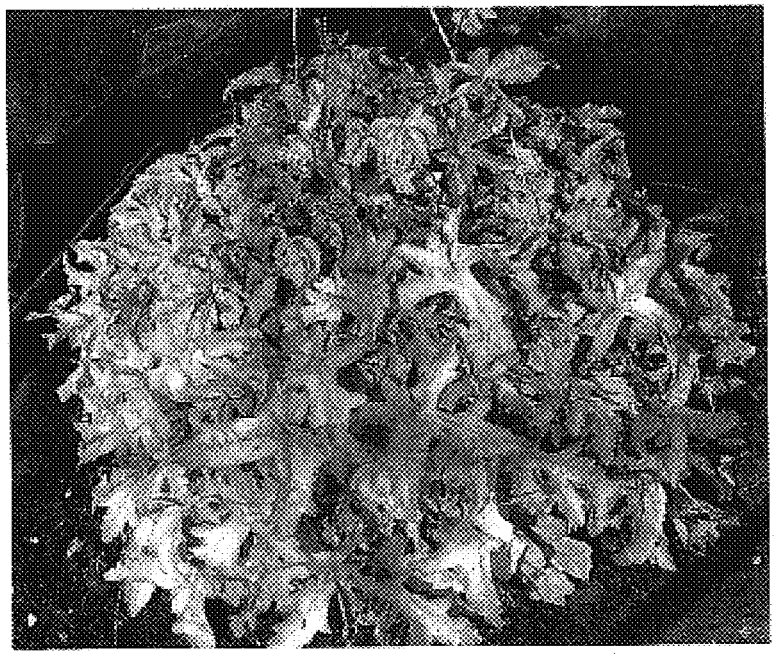
FIG. 1 shows the two year old plant in April growing in the ground grown in shade in Canby, Oreg.
Figure 2:
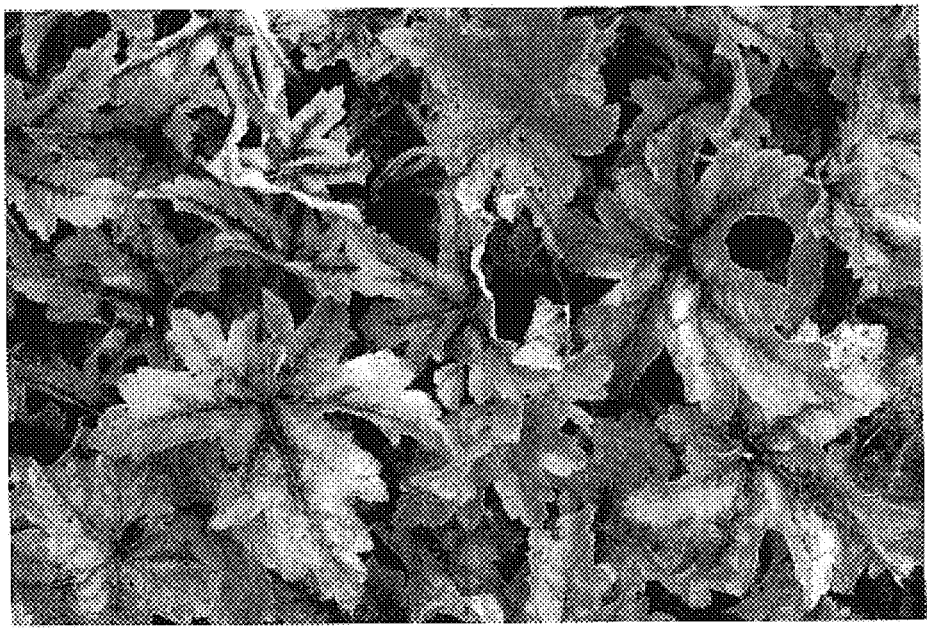
FIG. 2 shows a close up of the leaves in the summer.
Figure 3:
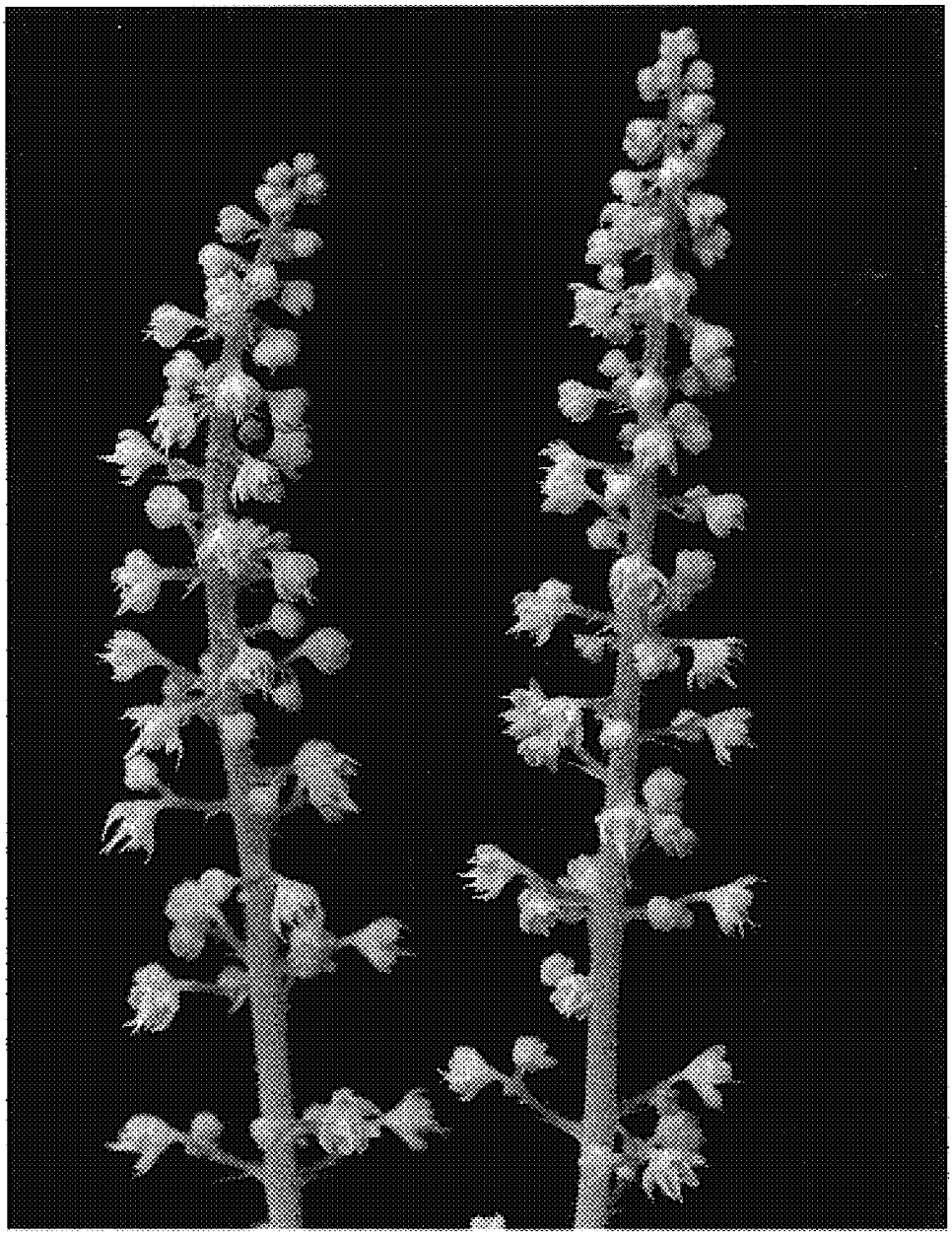
FIG. 3 shows a close up of the flowers in early spring.

The following is a detailed description of the new ×*Heucherella* hybrid based on observations of a three-year-old specimen grown in the ground in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Botanical denomination: ×*Heucherella*.sp.
Variety designation: 'HERTN041'.
Plant:
- *Type.*—Herbaceous perennial.
- *Form.*—Basal rosette.
- *Hardiness.*—USDA Zone 4.
- *Size.*—20 cm tall from the soil to the top of the foliage and 50 cm wide.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Ovate.
- *Lobing /division.*—3 to 5 main deeply cut lobes with each of these coarsely lobed, terminal lobe is the longest, two main laterals are often at a right angle to the main lobe.
- *Venation.*—Palmate.
- *Margins.*—Coarsely crenate.
- *Apex.*—Mucronulate.
- *Base.*—Cordate, slightly overlapping.

*Blade size.*—Ranges from 5 to 8 cm long and 5 to 6.7 cm wide.

*Surface texture.*—Glandular hairs mostly on back side.

*Petiole size.*—Ranges from 7 to 13 cm long and 2 mm wide.

*Petiole texture.*—Glandular hairs.

*Petiole color.*—Changes from Greyed Red 178A at the base to Yellow Green 145C near leaf blade.

*Leaf color.*—Leaves open in spring a yellow green with a speckled maroon pattern along veins and become greener with maturity. Spring leaves topside — Yellow Green 145A with speckles of Greyed Purple 187B. Mature leaves topside — Yellow Green 144A with minor speckling. Bottom side — Closest to Yellow Green 145A maturing to Yellow Green 146C.

Inflorescence:

*Type.*—Thyrse.

*Number of flowers.*—Ranges from 30 to 70 per thyrse.

*Size of inflorescence.*—13 cm long and 3 cm wide.

*Peduncle.*—Grows to 31 cm tall and 2 mm wide, with glandular hairs, and with 0 to 10 leaves (petiole at the bottom and sessile near the top, 5.5 to 1 cm long and 3 to 0.5 cm wide, deeply 5 parted to incised) and 0 to 2 branches. Color — Greyed Orange 176A maturing to Yellow Green 152A except near base where it is Greyed Orange 165A.

*Pedicel.*—Grows to 6 mm long, with glandular hairs, Greyed Orange 174A.

*Bloom period.*—Early April to late May.

Flower bud:

*Size.*—2 mm deep and wide.

*Description.*—Ovoid, side facing, glandular.

*Color.*—Greyed Yellow 160A.

Flower:

*Type.*—Perfect, sepals petaloid.

*Shape.*—Rotate.

*Size.*—4 mm wide and 3 mm deep.

*Petal description.*—5 in number, oblanceolate in shape, 1.5 mm long and 0.5 mm wide, Yellow White 158A.

*Calyx description.*—Rotate, 5 lobed, 5 mm wide and 3 mm deep, glandular on the outside and glabrous on the inside, Yellow White 158A.

*Stamen description.*—Conspicuously exerted, 10, sterile, thickened, Green Yellow 1D, no anthers.

*Pistil description.*—Green Yellow 1D overall, 2.5 mm long.

*Fragrance.*—None.

*Lastingness.*—A thyrse blooms for about 2 weeks on the plant.

Fruit, seed: None. The plant does not form fruit or seed.

*Fertility.*—Male and Female sterile.

Disease and pest tolerance: All *Heucherella* are susceptible to root weevils. No problems have been identified for this new cultivar.

COMPARISONS TO SIMILAR ×*HEUCHERELLA*

Compared to *Heucherella* 'Sunspot' (U.S. Plant Pat. No. 14,825), this new cultivar has leaves that are less gold colored and marked red at the veins and the leaf lobes are cut and jagged rather than round.

Compared to the seed parent, *Heuchera* 'Amber Waves', the new cultivar has foliage that is more of a yellow green than an amber color, and the leaves of the new variety are not ruffled and uncut like the seed parent.

I claim:

1. A new and distinct cultivar of ×*Heucherella* plant as herein illustrated and described.

* * * * *

UNITED STATES PATENT AND TRADEMARK OFFICE

CERTIFICATE OF CORRECTION

PATENT NO. : PP 17,634 P3
APPLICATION NO. : 11/088695
DATED : April 24, 2007
INVENTOR(S) : Gossett It is certified that error appears in the above-identified patent and that said Letters Patent is hereby corrected as shown below:

In the Specification:

Line 1, column 24, “sexual” should be --asexual--.

Signed and Sealed this

Twenty-ninth Day of April, 2008

JON W. DUDAS
*Director of the United States Patent and Trademark Office*